(12) United States Patent
Krutmann

(10) Patent No.: US 8,822,477 B2
(45) Date of Patent: Sep. 2, 2014

(54) USE OF OSMOLYTES OBTAINED FROM EXTREMOPHILIC BACTERIA FOR PRODUCING MEDICINE FOR THE EXTERNAL TREATMENT OF NEURODERMATITIS

(75) Inventor: Jean Krutmann, Wegberg (DE)

(73) Assignee: Bitop AG (DE)

( * ) Notice: Subject to any disclaimer, the term of this patent is extended or adjusted under 35 U.S.C. 154(b) by 267 days.

(21) Appl. No.: 10/563,586

(22) PCT Filed: Jul. 1, 2004

(86) PCT No.: PCT/EP2004/007134
§ 371 (c)(1),
(2), (4) Date: Dec. 13, 2006

(87) PCT Pub. No.: WO2005/002581
PCT Pub. Date: Jan. 13, 2005

(65) Prior Publication Data
US 2007/0122464 A1 May 31, 2007

(30) Foreign Application Priority Data
Jul. 3, 2003 (DE) .................................. 103 30 243

(51) Int. Cl.
*A61K 31/505* (2006.01)
*A61K 9/127* (2006.01)

(52) U.S. Cl.
USPC .......................................... 514/256; 424/450

(58) Field of Classification Search
USPC .......................................... 424/520, 400, 401
See application file for complete search history.

(56) References Cited

U.S. PATENT DOCUMENTS

| 5,894,019 A | 4/1999 | Hesse et al. |
| 6,060,071 A * | 5/2000 | Motitschke et al. .......... 424/401 |
| 6,602,514 B1 * | 8/2003 | Bunger et al. ................ 424/401 |
| 2004/0053860 A1 * | 3/2004 | Buchholz et al. ................ 514/27 |
| 2004/0220137 A1 * | 11/2004 | Sauermann ..................... 514/54 |

FOREIGN PATENT DOCUMENTS

| DE | 10133202 A1 * | 1/2003 |
| JP | 2002265327 | 9/2002 |
| JP | 2002302444 | 10/2002 |
| WO | WO00/51605 | 9/2000 |
| WO | WO03/005980 | 1/2003 |
| WO | WO03/005988 | 1/2003 |
| WO | WO03/051385 | 6/2003 |

OTHER PUBLICATIONS

Hanifin et al., "Effects of a Low-potency Corticosteroid Lotion Plus a Moisturizing Regimen in the Treatment of Atopic Dermatitis," Current Therapeutic Research, vol. 59, No. 4, Apr. 1998, pp. 227-233.*
Touitou et al., "Liposomes as Carriers for Topical and Transdermal Delivery," Pharmaceutical Sciences, vol. 83, No. 9, Sep. 1994, pp. 1189-1203.*
Lodén et al., "Improvement in skin barrier function in patients with atopic dermatitis after treatment with a moisturizing cream (Canoderm®)," British Journal of Dermatology, 1999; 140: pp. 264-267.*
Nghiem et al., "Tacrolimus and pimecrolimus: From clever prokaryotes to inhibiting calcineurin and treating atopic dermatitis," J. Am. Acad. Dermatol., Feb. 2002, 6(2): pp. 228-241.*
dictionary.com definition of "irritated."*
Dictionary.com definition of "irritated" accessed on Apr. 10, 2012.*

* cited by examiner

*Primary Examiner* — Sreeni Padmanabhan
*Assistant Examiner* — Jody Karol
(74) *Attorney, Agent, or Firm* — Berliner & Associates

(57) ABSTRACT

The invention relates to the use of osmolytes, in particular ectoine and hydroxyectoine, as well as their pharmacologically compatible salts and/or derivatives having equivalent effects, for producing dermatological preparations such as tinctures, lotions, O/W emulsions, W/O emulsions, creams, ointments, hydrogels or sprays for the topical prophylaxis, care and/or treatment of neurodermatitis.

9 Claims, No Drawings

USE OF OSMOLYTES OBTAINED FROM EXTREMOPHILIC BACTERIA FOR PRODUCING MEDICINE FOR THE EXTERNAL TREATMENT OF NEURODERMATITIS

BACKGROUND OF THE INVENTION

Extremophilic bacteria are extraordinary microorganisms capable of existing and reproducing under the most extreme conditions, e.g. in the presence of extremely high salt concentrations of up to 200 g of sodium chloride per liter and temperatures ranging between 60 and 110° C. Such habitat conditions would cause the immediate death of normal (mesophilic) organisms or would at least lead to an extensive damage of cellular structures.

In recent years comprehensive research efforts have therefore been made to identify the biochemical components that are the reason for and bring about the remarkable thermal, chemical and physical stability of the cell structures found in extremophilic organisms.

The high temperature stability of cell structures is—to a remarkable extent—due to low-molecular organic substances present in the intracellular environment which are known as osmolytes or compatible solutes. Osmolytes found in extremophilic microorganisms are not produced by human or animal cells. Recently, various newer osmolytes have been identified for the first time in extremophilic microorganisms. These include, for example, ectoine, hydroxyectoine, firoin, firoin-A, diglycerolphosphate, cyclic diphosphoglycerate, 1,3-dimannosyl-myo-inositol-phosphate (DMIP) and diinositol phosphate. All of them are won from extremophilic microorganisms, then refined and cleaned (refer to EP-A 94 903 874; EP-A 98 121 243; DE-A 100 47 444), thus forming a known group of low-molecular substances offering protection for otherwise sensitive cells. In some cases it could be shown already that these compounds in the field of cosmetics contributed to the protection of skin cells against external stress conditions such as heat and dryness (refer to U.S. Pat. No. 6,267,973).

It has occasionally been proposed to preferably make use of topical pharmaceutical products aimed at protecting the skin against externally induced stress or treating illnesses caused by the enzymatic decomposition of tissue structures (refer to DE-A 100 06 578). Aside from other diseases of general nature diseases of the immune system, autoimmune related diseases, inflammatory processes as well as acute and chronic inflammations were mentioned in that context. DE-A 198 34 816 which also proposes the use of ectoine and other osmolytes relates to cosmetic formulations offering skin protection against UV radiation and said products should, moreover, have a stabilizing effect on the nucleic acids of human skin cells.

The osmolyte ectoine was also employed as moisturizer in cosmetic preparations with the aim of protecting healthy, clinically inconspicuous human skin against the detrimental effects of ultraviolet solar radiation (EP-A 19 990 941). As a result of in-vitro and in-vivo investigations it has been assumed that the cosmetic effect of ectoine is based, inter alia, on the fact that the functions of epidermal Langerhans cells as well as epidermal keratinozytes and dermal fibroblasts are influenced in such a way that they are better protected against the proinflammatory effects of UV radiation which would give rise to sunburns.

The production of a pharmaceutical preparation intended for the general treatment of skin diseases by means of osmolytes, in particular ectoine or hydroxyectoine, is known from EP-A 0 887 418 which was previously filed by the applicant Bitop AG itself. It has been assumed in that context that these agents contribute towards stabilizing enzymes and other biomolecules and as a result of this can promote the stabilization of denaturizing conditions.

In laid-open patent applications DE-A 199 33 460, DE-A 199 33 461, DE-A 199 33 463 und DE-A 199 33 466 it has been proposed due to their antioxidative effect to use ectoines as free-radical scavengers and in this way protect the skin, especially against ageing accelerated and intensified due to solar radiation. Moreover, undesirable skin states resulting from oxidative phenomena should also be avoided in this manner. Based on premises similar to those proposed in the publications last referred to WO 01/72287 describes the use of ectoines in conjunction with the treatment of UV induced immunosuppression.

Neurodermatitis, also termed endogenous eczema or atopic dermatitis, is still a very frequent skin disease which due to lack of suitable treatment methods often continues for years or even decades and is characterized by a persistent itchiness which can hardly be combated effectively and leads to patients suffering enormous psychological strain. One of the assumed causes for this is an excessively dry and sensitive skin showing a strong tendency towards inflammation. The disease very often commences during childhood or early adolescence. Newer studies have shown that up to 12% of an age group may be affected.

Clinically speaking, relatively vaguely limited papular, weeping, desquamating, excoriating, partially superinfected eczematic skin changes will develop which are primarily found in the face, decollete, on the neck and large joint areas but may as well affect the entire integument. Furthermore, should the disease become chronic a lichenification of the skin changes can frequently be observed. The so-called infant eczema often occurs as early as in the third month of life. Many cases of this disease are encountered during the playing and school age. Especially, children will constantly scratch itching areas thus breaking the skin open and provoking inadvertent superinfections that are difficult to treat.

Nothing certain can yet be said about possible causes of this serious disease. Relevant opinions held by experts in this field vary. Aside from other, not yet exactly clarified factors a disorder of the body's defense system may also be attributable to the appearance of the disease. Moreover, assumptions are also that congenital factors may at least promote the outbreak of the disease. It has also been found that patients suffering from neurodermatitis show allergic reactions to environmental substances otherwise considered harmless.

Perforce, treatment has hitherto rather been focused on remedying the symptoms, in particular treating the unpleasant skin phenomena and itchiness. As a rule, the topical treatment involves the use of glucocorticosteroids or calcineurin inhibitors and/or a controlled exposure to ultraviolet light. Due to the lack of a curative therapy the symptomatic treatment strategies presently adopted address various aspects intended to complement one another. For example, because of skin dryness and an apparent insufficiency of the skin's lipometabolism treatment methods include cold compresses but also fatty ointments or oil baths. This embraces, for instance, the treatment with high-dosed evening primrose seed oil (EPOGAM® capsules). The intention here is to introduce into the skin gamma-linolenic acid via the metabolism. During the treatment of the inflamed skin areas antiinflammatory active agents are employed. Antihistamine drugs shall alleviate the itchiness. Although cortison preparations alleviate occurring skin irritations they will not lead to healing the disease directly. Antibiotics may also be needed for the treatment of infected skin areas.

Judging from the state of the art as described hereinbefore it is evident that a definite treatment pattern for the treatment of neurodermatitis has not yet been established and in each individual case decisions must be taken tailored to the respective disease pattern as to which of the above mentioned methods and which of the numerous possible combinations are most promising. For that reason, any advancement and every novel alternative in therapy must be acclaimed, especially as long as science has not yet agreed on an equally shared opinion about the actual causes of this serious disease and as not a single one of the agents so far proposed has proved successful in all aspects. When carefully weighing the therapy measures known so far it may only be assumed that as an individual method a glucocorticosteroid treatment is considered the most effective therapy, but nevertheless one that brings with it a great number of adverse effects. Comparably effective here is the therapy employing calcineurin inhibitors which, however, has a disadvantage in that certain risks of cancer may exist when the therapy is accompanied by a simultaneous exposure to UV or sunlight.

BRIEF SUMMARY OF THE INVENTION

It is thus the objective of the present invention to make available a safe agent for the treatment of neurodermatitis which in respect of effectiveness is comparable to the one using glucocorticoids or calcineurin inhibitors but has less adverse effects.

It has now been found that for the treatment of neurodermatitis the topic application of osmolytes, in particular ectoine and hydroxyectoine, has shown a surprisingly high effectiveness.

DETAILED DESCRIPTION OF THE INVENTION

In comparison to a placebo treatment an unexpectedly accelerated healing of affected skin changes was achieved during treatment with osmolytes, especially ectoine and hydroxyectoine. Aside from the effects occurring quickly this means a substantial medical advancement, particularly when applied on a long-term basis, because the known and numerous adverse effects of glucocorticoids can practically be avoided entirely by the invention. Because the osmolytes of the invention are practically free from adverse effects as far as is presently known this may also be considered a major enhancement of the safety of pharmaceutical preparations. Another noteworthy aspect is that the effectiveness of a calcineurin inhibitor could be significantly surpassed by the agents proposed by the invention. As already explained, an increased danger of skin cancer is generally associated with the use of calcineurin inhibitors when their application is simultaneously accompanied by an exposure to sunlight or artificial UV light. The present invention now proposes and thus makes available an agent that does not involve this risk and is even more effective.

Object of the invention is the use of osmolytes as well as their derivatives and/or pharmacologically compatible salts for the production of dermatological preparations for the topical prophylaxis, treatment and/or tending of neurodermatitis.

Some of the active agents according to the invention are weak bases or acids and for that reason may, in some instances even preferably, be employed in their pharmacologically most compatible neutral salt form.

Pharmacologically compatible salts embrace alkaline or alkaline-earth salts, in particular potassium, sodium, magnesium and calcium but also salts with organic bases such as, for example, with non-toxic aliphatic or aromatic amines.

Should nitrogen atoms be present in the active agent molecule and the basic nature is predominant, salts with pharmacologically unobjectionable organic or inorganic acids are formed such as for example acetic acid, citric acid, tartaric acid, mandelic acid, malic acid, lactic acid, hydrochloric acid, hydrobromic acid, sulfuric acid or phosphoric acid.

Preferred osmolytes are ectoine, hydroxyectoine as well as their derivatives and salts having similar effects. Also preferred are combination preparations containing one of the active agents or both active agents coexisting and including further active agents if thought expedient.

Derivatives having equal effects are compounds that in comparison to the basic structures of the osmolytes mentioned hereinbefore show structural differences, in particular of the functional groups and substituents, but have equivalent or similar effects within the scope of the invention. In the event of hydroxyectoine for example relevant alkoxyl groups may form from the hydroxyl group with saturated or unsaturated, straight-chain or branched $C^1$ to $C^4$ alkyl groups. With $C^1$ to $C^4$ carboxylic acids relevant esters are formed. From the carboxyl group amides form which in turn may comprise saturated or unsaturated, straight-chained or branched $C^1$ to $C^4$ alkyl groups attached to the nitrogen atom. Using relevant $C^1$ to $C^4$ alcohols effective esters are obtained. The carboxylate group may thus be substituted by a carbonyl, sulfonyl or sulfonylate group. Relevant modifications of the other osmolytes mentioned may be brought about in an analogous manner with the effect being maintained or even enhanced.

Generally speaking, the active agents or combinations thereof according to the invention may be processed galenically in a known manner making use of customary auxiliary skin-compatible and pharmacologically unobjectionable substances and additives. Such additives may be, inter alia, emulgators, solvents, thickeners, fillers, stabilizers, preservation agents or antioxidants.

Moreover, surfactants such as polyoxy ethylene sorbitan acid and esters or salts of bile acid may also be used to improve bio-availability, if thought necessary. In the present case, however, it is basically recommendable that just a minimum of auxiliary substances be employed because of the existing allergy potential and general sensitivity of the diseased skin.

Aside from the osmolytes proposed by the present invention further active agents suitable for treatment may be added. Among such agents are, for example, antiphlogistics as well as antibacterial, fungistatic or fungicide agents, provided these do not impede the application and use proposed by the invention as a result of the danger of allergic phenomena or known sensitivity of the usually predamaged skin as described above.

If so desired, dispersion agents such as, for example, polyacrylate, lignin, tannates or derivatives thereof may be added to enable insoluble auxiliary substances to be incorporated. For example, colloidal silicon oxide may be used as thickening agent. Hydrogels can be produced with the aid of hydrophilic organic solvents such as glycerine, glycol or aliphatic alcohols, for example. Furthermore, it is within the scope of the invention to use the active agents according to the invention in the form of active-substances containing microsomes or liposomes or as liposomally or microsomally capsuled active agent with microsomally capsuled repair enzymes and so-called Actives, if necessary in parallel with other auxiliary substances and further active agents.

The active agents according to the invention may be processed to obtain practically all forms of preparations suited for application to the human skin. Such forms of preparations are, for example, tinctures, hydrogels, oil-in-water emulsions, water-in-oil emulsions, lotions, creams, ointments or sprays. The concentration of the active agents usually ranges between 0.01 and 20 percent by weight.

The most favorable concentration is assumed to range between 0.1 and 2 percent by weight in relation to the weight of the carrier material used.

The following examples serve to elucidate the invention but are in no way whatsoever meant to limit its scope.

Example 1

W/O Emulsion

| Constituents | Percentage by weight |
| --- | --- |
| Water | 85.0 |
| Ectoine | 1.0 |
| Fat basis | 10.3 |
| Polyvalent alcohols | 3.2 |
| Solid thickeners | 0.3 |
| Preservative agents | 0.2 |

Example 2

W/O Emulsion

| Constituents | Percentage by weight |
| --- | --- |
| Water | 85.0 |
| Hydroxyectoine | 1.0 |
| Fat basis | 10.3 |
| Polyvalent alcohols | 3.2 |
| Solid thickeners | 0.3 |
| Preservative agents | 0.2 |

Example 3

W/O Emulsion

| Constituents | Percentage by weight |
| --- | --- |
| Water | 85.0 |
| Ectoine/hydroxyectoine 1:1 | 1.0 |
| Fat basis | 10.3 |
| Polyvalent alcohols | 3.2 |
| Solid thickeners | 0.3 |
| Preservative agents | 0.2 |

Example 4

Cream

| Constituents | Percentage by weight |
| --- | --- |
| Water | 61.7 |
| Ectoine | 0.5 |
| Fat basis | 32.8 |
| Polyvalent alcohols | 4.0 |
| Solid thickeners | 0.5 |
| Preservative agents | 0.5 |

Example 5

Cream

| Constituents | Percentage by weight |
| --- | --- |
| Water | 61.7 |
| Hydroxyectoine | 0.5 |
| Fat basis | 32.8 |
| Polyvalent alcohols | 4.0 |
| Solid thickeners | 0.5 |
| Preservative agents | 0.5 |

Example 6

Cream

| Constituents | Percentage by weight |
| --- | --- |
| Water | 61.5 |
| Ectoine/hydroxyectoine 1:1 | 1.0 |
| Fat basis | 32.5 |
| Polyvalent alcohols | 4.0 |
| Solid thickeners | 0.5 |
| Preservative agents | 0.5 |

The invention claimed is:

1. A method of treating neurodermatitis patients comprising topical application on affected skin of a dermatological preparation comprising an osmolyte or a pharmacologically compatible salt thereof to a patient in need thereof, wherein the osmolyte is ectoine or hydroxyectoine or a pharmacologically compatible salt thereof, wherein said osmolyte results in accelerated healing of the affected skin.

2. The method of claim 1, wherein the dermatological preparation is a tincture, lotion, O/W emulsion, W/O emulsion, cream, ointment or a hydrogel or spray comprising auxiliary substances.

3. The method of claim 2, wherein the dermatological preparation is an ointment, cream or lotion, comprising liposomes containing the osmolyte.

4. The method of claim 3, wherein the dermatological preparation is an ointment, cream or lotion containing the osmolyte liposomally capsuled.

5. The method of claim 1, wherein the dermatological preparation contains additional active agents.

6. The method of claim 5, wherein the dermatological preparation contains an active agent selected from analgetics, antiphlogistics, antipruritic substances, antibiotics, fungistats and fungicides.

7. The method of claim 5 or 6, wherein the additional active agent is a calcineurin inhibitor.

8. The method of claim 1, wherein the dermatological preparation consists essentially of ectoine or hydroxyectoine or a pharmacologically compatible salt thereof.

9. The method of claim 1, wherein the dermatological preparation comprises ectoine or hydroxyectoine or a pharmacologically compatible salt thereof in the absence of a glucocorticoid.

\* \* \* \* \*